United States Patent [19]
Hodges

[11] Patent Number: 5,507,793
[45] Date of Patent: Apr. 16, 1996

[54] NON-CONSTRICTING NECK WRAP

[76] Inventor: Terry L. Hodges, 920 W. Pinhook Rd., Lafayette, La. 70503

[21] Appl. No.: 281,418
[22] Filed: Jul. 27, 1994
[51] Int. Cl.$^6$ ........................................ A61F 7/00
[52] U.S. Cl. ............................ 607/109; 607/114
[58] Field of Search ................ 607/96, 108–112, 607/114

[56] References Cited

U.S. PATENT DOCUMENTS

| | | | |
|---|---|---|---|
| 3,889,684 | 6/1975 | Lebold | 607/109 |
| 4,576,169 | 3/1986 | Williams | 607/109 |
| 4,641,655 | 2/1987 | Abt . | |
| 4,676,247 | 6/1987 | Van Cleve . | |
| 4,742,827 | 5/1988 | Lipton | 607/109 |
| 4,805,619 | 2/1989 | Swearingen . | |
| 4,832,030 | 5/1989 | DeCanto . | |
| 5,005,374 | 4/1991 | Spitler . | |
| 5,088,549 | 2/1992 | Schneider . | |
| 5,247,928 | 9/1993 | Stilts, Jr. | 607/109 |
| 5,295,949 | 3/1994 | Hathaway | 607/109 X |

Primary Examiner—Angela D. Sykes
Attorney, Agent, or Firm—Roy, Kiesel & Tucker

[57] ABSTRACT

A neck wrap comprising a wrap member and a fastening means is described. The wrap member includes a center section and two extended sections. The center section is of a first predetermined width and has a first and second end and a heat transfer unit retaining means, located between the first and second ends, which has dimensions sufficient to allow a desired heat transfer unit to be inserted and retained within the heat transfer unit retaining means during use. Each of the two extended sections is of a second predetermined width greater than the first predetermined width of the center section. The extended sections are connected at the first and second end of the center section in a manner such that a flap portion is created on each of the extended sections of sufficient width to allow the extended portions to be attached together without constricting the throat area of the user when the neck wrap is in use. One of the extended sections is attached to the first end of the center section, and the other extended section is attached to the second end of the center section. Each of the extended sections is of sufficient length to permit moisture removal from the head and arms of a wearer. The fastening means includes a first and second interlocking segment. The first interlocking segment is attached to one of the flap portions and the second interlocking segment is attached to the other the flap portion.

4 Claims, 4 Drawing Sheets

NON-CONSTRICTING NECK WRAP

BACKGROUND OF THE INVENTION

The invention relates generally to neck wraps and more particularly to neck wraps having sectionalized pockets which are securable about the neck without unduly constricting the throat area of the wearer.

Neck wraps are used for a variety of purposes, including the application of heat and cooling to the neck area. The application of heating and cooling to the neck area is beneficial because the neck region is a primary location for heat loss. It is often the case that outdoor activities, such as fishing and sporting events, take place under temperature conditions which make it difficult to maintain body temperatures at a safe and comfortable level. It would be a benefit, therefore, while pursuing such activities, to provide either heating or cooling to the neck area to maintain a safe and comfortable body temperature.

The principal problem associated with wearing a conventional neck wrap while pursuing sporting activities is the constriction of the area about the throat caused by securing the neck wrap in an effort to maintain the neck wrap in contact with the neck. It would be desirable to have a neck wrap which could be secured about the neck which would not constrict the throat area.

SUMMARY OF INVENTION

Therefore, it is an object of the present invention to provide a neck wrap which is securable about the neck without unduly restricting the throat area during use.

It is another object of the invention to provide such a neck wrap which is easily filled with ice for cooling the neck of the user.

Accordingly, a neck wrap comprising a wrap member and a fastening means is described. The wrap member includes a center section and two extended sections. The center section is of a first predetermined width and has a heat transfer unit retaining means, located between the first and second ends, which has dimensions sufficient to allow a desired heat transfer unit to be inserted and retained within the heat transfer unit retaining means during use, and a first and second end. Each of the two extended sections is of a second predetermined width greater than the first predetermined width of the center section. The extended sections are connected at the first and second ends of the center section in a manner such that a flap portion is created, on each of the extended sections, of sufficient width to allow the extended portions to be attached together by the fastening means without constricting the throat area of the user when the neck wrap is in use. One of the extended sections is attached to the first end of the center section, and the other extended section is attached to the second end of the center section. Each of the extended sections is of sufficient length to permit moisture removal from the head and arms of a wearer.

The fastening means allows the center section of the neck wrap to be secured about the neck during use. The fastening means includes a first and second interlocking segment. The first interlocking segment is attached to one of the flap portions and the second interlocking segment is attached to the other flap portion.

In a preferred embodiment of the invention the wrap member is constructed of a soft absorbent material such as terry cloth. In another preferred embodiment of the invention, the heat transfer unit retaining means is a plurality of sealable pockets formed within the center section. Each of the pockets includes an integrally formed flap and is dimensioned to allow insertion of a desired heat transfer unit. A third embodiment of the invention includes a U-shaped envelope which is insertable into the wrap member, and which is refillable with a heat transfer medium such as ice.

The simplicity of the neck wrap design lends itself to a cost effective manufacture. In addition, the compartmentalized design allows the user to select a desired location on the neck in the event that it is not desired to utilize all the pockets at the same time. When the climate is warm, cooling packs may be added to cool the neck. Conversely, when the climate is cool, heat packs may be added to warm the neck.

BRIEF DESCRIPTION OF THE DRAWINGS

The drawings and detailed description of the preferred embodiments will illustrate the advantages of the instant invention, wherein.

DESCRIPTION OF THE PREFERRED EMBODIMENT

Figure 1:
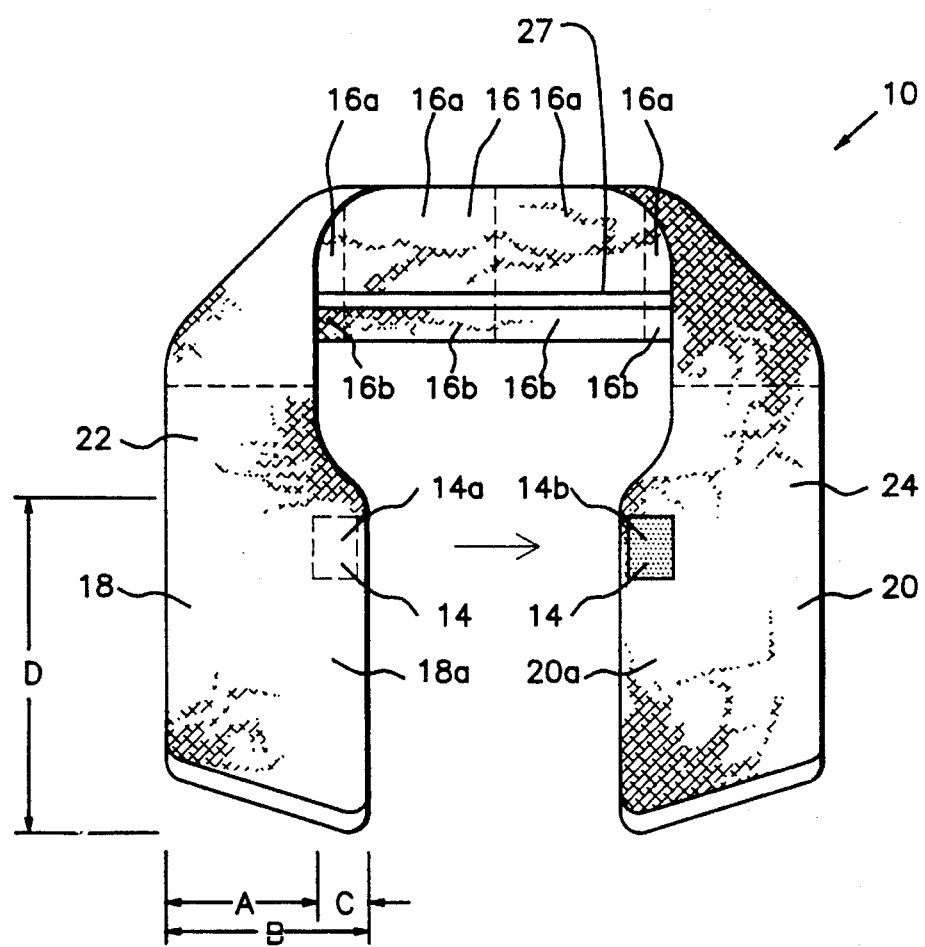
FIG. 1 is a perspective view of an embodiment of the invention, shown unfastened.
Figure 5:
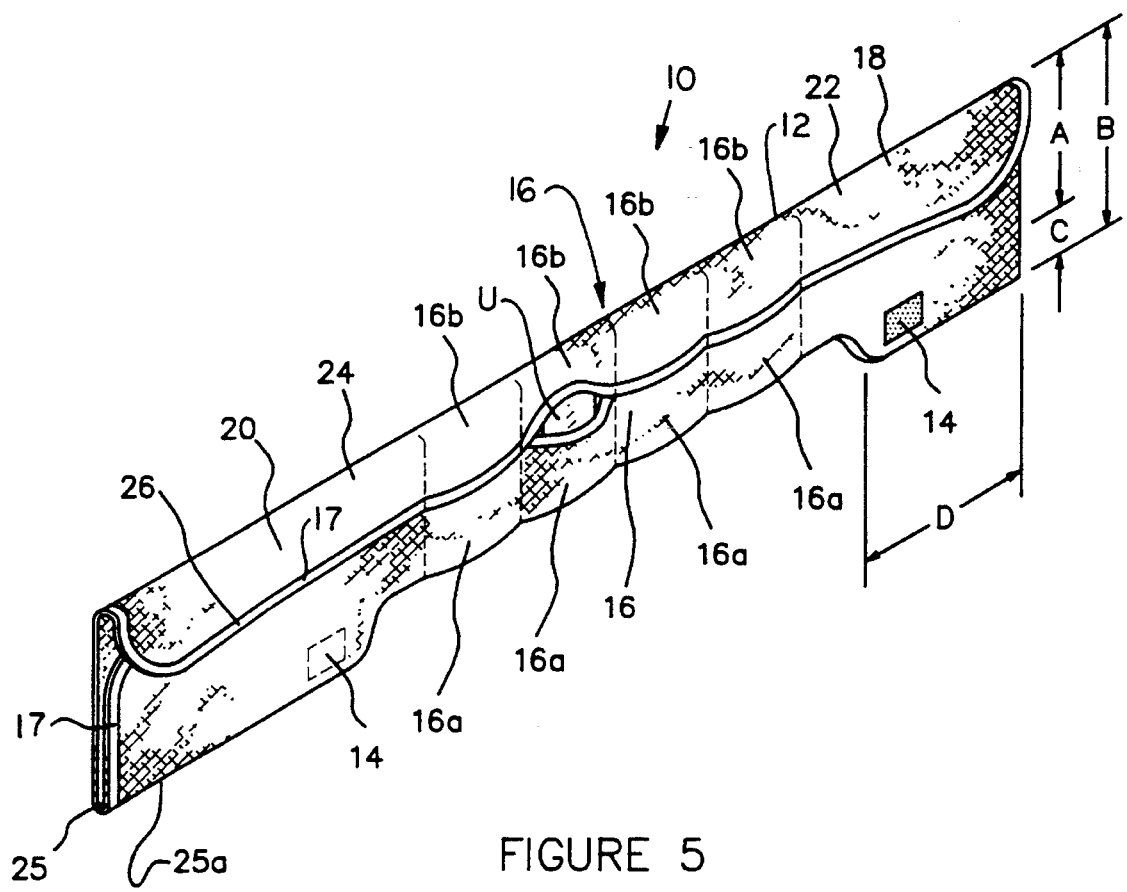
FIG. 5 is an extended perspective view of an embodiment of the invention, shown unfastened.

FIGS. 1 and 5 show an embodiment of the neck wrap 10 of the present invention. The neck wrap in this embodiment includes a wrap member 12, and a fastening means 14. Wrap member 12 is constructed of a flexible and absorbent material, and includes a center section 16 and two extended sections 18, 20. In this preferred embodiment, wrap member 12 is constructed of a soft, absorbent material, preferably terry cloth.

Center section 16 has first end 22 and a second end 24, and is of a first predetermined width A which corresponds to the length of a typical neck. In this embodiment width A is preferably about three and one-half inches. A heat transfer unit retaining means is located within the center section 16. The heat transfer unit retaining means preferably includes a plurality of closable pockets 16a, each having a pocket flap 16b which is integrally formed with the center section 16. The embodiment shown includes four sectionalized pockets 16a, however, it is contemplated that a fewer or greater number of pockets 16a may be incorporated within the center section 16.

Figure 2:
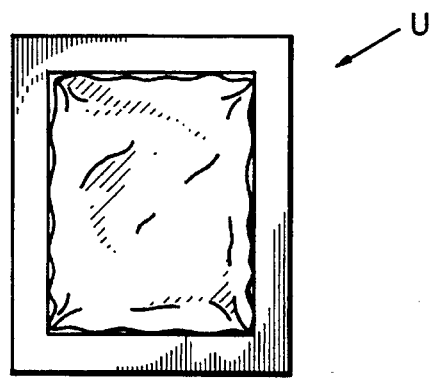
FIG. 2 is a side view of an exemplary heat transfer unit.

Each pocket 16a is dimensioned to allow a desired heat transfer unit, U, to be inserted and retained therein. "Heat transfer unit" is used herein to mean any removable element which will supply or absorb heat at a rate which will not damage the tissues of the neck. An example of a desired heat transfer unit U is shown in FIG. 2. The heat transfer unit U illustrated is an air activated heating pad which will maintain, upon exposure to air, an even temperature of about 135 degrees Fahrenheit for approximately ten hours. Although a heat transfer unit U which supplies heat is used for exemplary purposes, it is to be understood that heat transfer units U which absorb heat, such as cooling packets containing ice and other cooling devices, are equally suitable for use in neck wrap 10.

Each of the two extended sections 18,20 is of a second predetermined width B which is greater than width A of center section 16. In the embodiment shown width B is preferably about five inches. Extended sections 18, 20 are attached to first end 22 and second end 24, respectively, in a manner such that flap portions 18a, 20a are created on each of extended sections 18, 20. Each flap portion 18a,20a has a width C sufficient to allow attachment of fastening means 14 thereto. In the embodiment shown, width C is preferably about one and one-half inches. Each extended section 18, 20 is of a length D which is sufficient to permit the user to contact his/her head and arms with a portion of extended section 18,20. In the embodiment shown, D is preferably about eleven inches. Extended sections 18,20 are particularly important when neck wrap 10 is used with cooling packets U, allowing the user to wipe his/her hands and face free of perspiration.

Fastening means 14 includes a first interlocking segment 14a and a second interlocking segment 14b for securing center section 16 about the neck. Although any two-part interlocking fastening means known in the art is sufficient to practice the invention, a Velcro™ hook and adhesive pile type fastener is preferred. First interlocking segment 14a is attached to one of the flap portions 18a, 20a and the second interlocking segment 14b is attached to the other flap portion 18a, 20a.

Locating the interlocking segments 14a, 14b on the flap portions 18a, 20a eliminates constriction around the throat when the neck wrap is secured about the neck of a user and allows the extended sections 18, 20 to drape vertically down the chest of the user in a smooth, even fashion. The smooth even drape of the extended sections 18, 20 permits the user to comfortably place the extended sections 18,20 beneath another garment. In the embodiment shown, the first interlocking segment 14a is attached to flap portion 18a, and the second interlocking portion 14b is attached to flap portion 20a.

Figure 3:
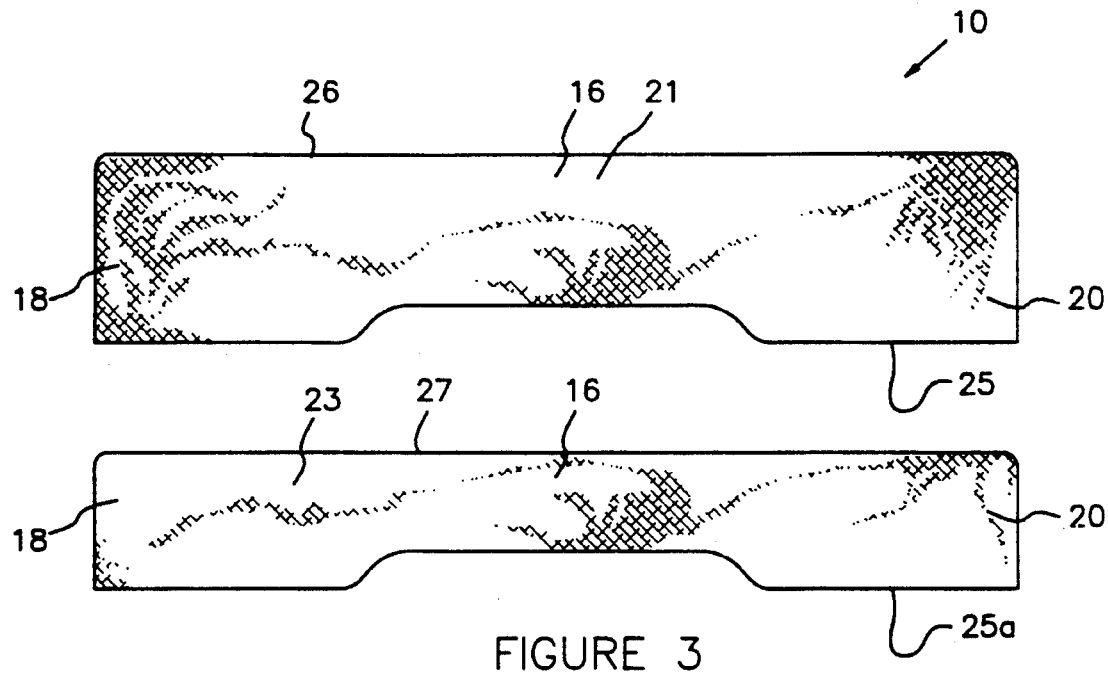
FIG. 3 is a side view of an unconstructed embodiment of the wrap member.

FIG. 3 shows an embodiment of the neck wrap 10 with the wrap member sections 21, 23 in a preconstructed state. The center section 16 of the wrap member 12 is unstitched. The extended sections 18,20 of the wrap member 12 are unfolded. The neck wrap 10 is constructed by stitching edges 25 and 25a together and then folding the edge 26 under edge 27 into the position shown in FIG. 1 forming flaps 16b. A hem 17 is preferably formed on the edges of flaps 16b, pockets 16a and the ends of the neck wrap 10, as shown in FIG. 1. Construction of the wrap member 12 is then completed by stitching across the width A of the center section 16 to form the sectionalized pockets 16a. The neck wrap 10 is then completed by stitching the interlocking segments 14a, 14b into position on the flap portions 18a, 20a as illustrated in FIG. 1.

Figure 4:
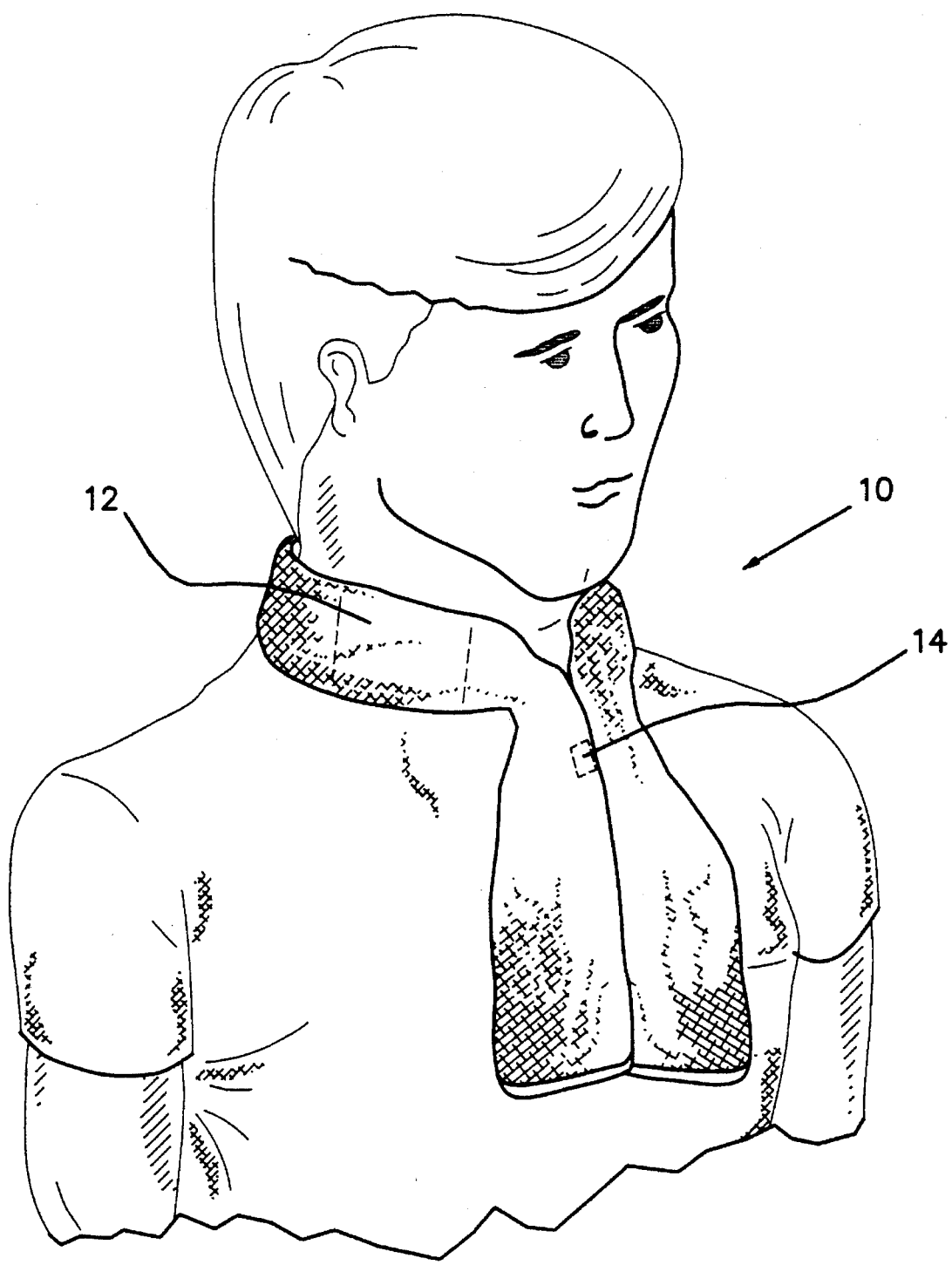
FIG. 4 is a perspective view of an embodiment of the neck wrap of the invention as it would appear when wrapped about the neck of a wearer.

In use, the sectionalized pockets 16a of the neck wrap 10 are filled with desired heat transfer unit U. The center section 16 is then placed across the back of the neck and the interlocking segments 14a, 14b are locked together in the manner shown in FIG. 4, securing the neck wrap 10 about the neck.

Figure 6:
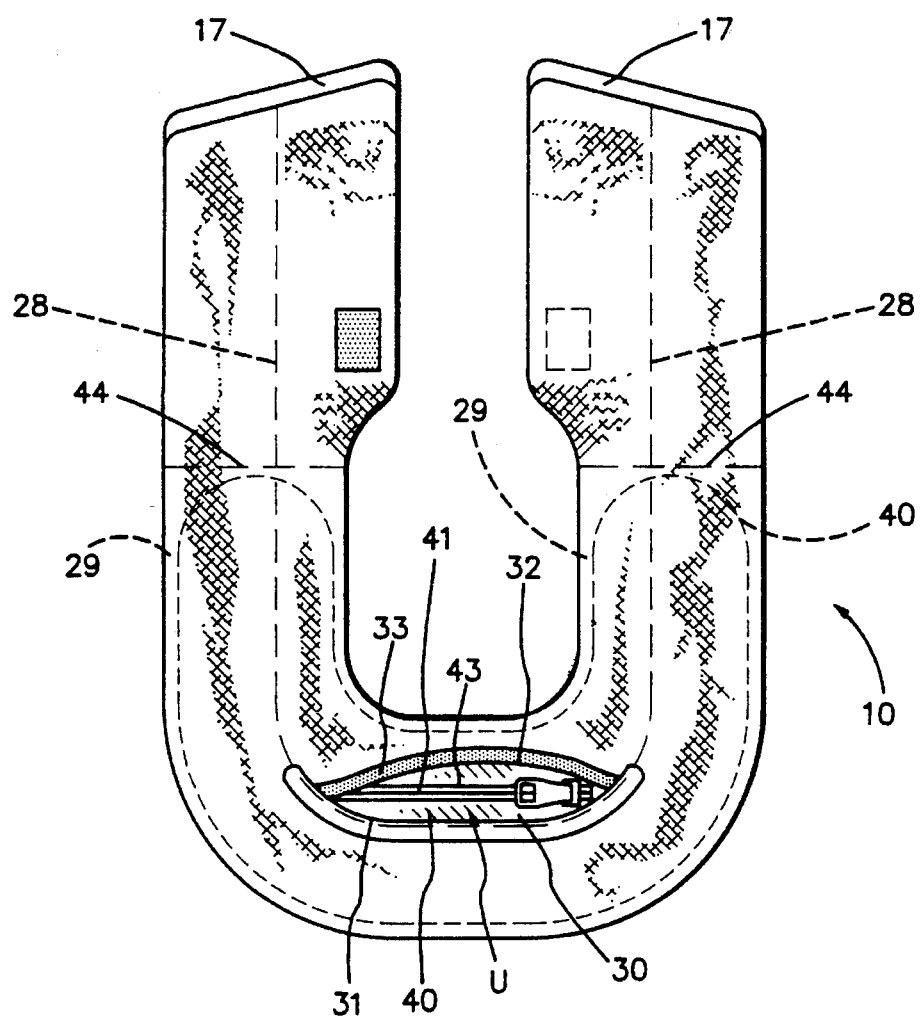
FIG. 6 is a top view of an alternate embodiment of the invention, shown unfastened.
Figure 7:
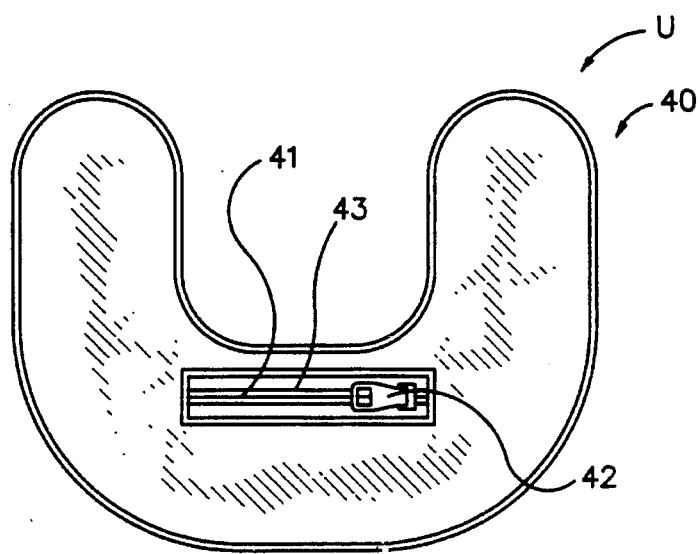
FIG. 7 is a top view of an alternate heat transfer unit for use with the embodiment shown in FIG. 6.

An alternate embodiment of the invention is shown in FIGS. 6 and 7. The embodiment shown is particularly useful during hot weather. In construction, edge 26 is folded over and overlaps with edge 27, as shown in FIGS. 1 and 3. However, a continuous lengthwise stitch 28 (see FIG. 6) is made to form an enlarged U-shaped pocket 29. On the reverse side, an opening 30 is formed, having overlapping edges 31,32. Preferably, edges 31,32 are closeable with a hook and adhesive pile fastener surface 33. Stop stitches 44 across neck wrap 10 form the ends of pocket 29. Pouch 40 is shown in greater detail in FIG. 7. Pouch 40 is preferably formed as a U-shaped envelope constructed of waterproof material, such as polyvinyl chloride. A sealable access opening 41 is provided, into which a heat transfer medium, such as ice, may be inserted. Access opening 41 is preferably sealable by a recloseable pressure seal 43 having a closure member 42 such as a slider, or zipper, as shown. When pouch 40 is sealed, it contains the ice and water, generally protecting the user from leakage during use. The seal is formed when interlocking edges (preferably a heavy-duty "tongue and groove" closure) of opening 41 are forced together. Although preferable of a heavier weight material, pressure seal 43 functions similarly to the typical seals of plastic storage bags, such as Zip-Loc™ storage bags. The slider 42 facilitates closure and assures a better seal. Pouch 40 may be filled with ice, and refilled when the ice melts. This feature is advantageous in that ice is readily available during most outdoor uses of the invention 10. Thus, after an extended period of use, the user simply empties water from pouch 40 and refills it with ice from an available ice chest or other container. The U-shaped design of pouch 40 provides a means to maintain the neck wrap 10 in position around the user's neck, as well as a cushion as the ice inside pouch 40 melts.

Although a preferred embodiment of the invention has been described herein, it should be appreciated that variations and modifications may be made thereto without departing from the spirit of the invention claimed.

What is claimed is:

1. A neck wrap comprising:

a wrap member comprising a center section, having first and second ends, said ends being of sufficient length and width to allow said ends to be attached together without constricting the throat area of a user when said neck wrap is in use; and a heat transfer unit retaining means comprising a closeable pocket formed within said center section, said pocket having an integrally formed flap and having dimensions sufficient to allow a heat transfer unit to be positioned therein, said heat transfer unit further comprising a U-shaped pouch having a sealable access opening therein;

a fastening means, having first and second interlocking segments for securing said center section about the neck, said first interlocking segment being attached to one of said ends and said second interlocking segment being attached to the other of said ends.

2. The neck wrap of claim 1, wherein said sealable access opening is provided with a recloseable pressure seal.

3. The neck wrap of claim 2, wherein said recloseable pressure seal includes a closure member.

4. The neck wrap of claim 3, wherein said closure member comprises a slider.

* * * * *